United States Patent
Chuckowree et al.

(10) Patent No.: US 7,781,433 B2
(45) Date of Patent: *Aug. 24, 2010

(54) PHARMACEUTICAL COMPOUNDS

(75) Inventors: Irina Chuckowree, Slough (GB); Adrian Folkes, Slough (GB); Tim Hancox, Slough (GB); Stephen Shuttleworth, Slough (GB)

(73) Assignee: Piramed Limited, Slough, Berkshire (GB)

( * ) Notice: Subject to any disclaimer, the term of this patent is extended or adjusted under 35 U.S.C. 154(b) by 583 days.

This patent is subject to a terminal disclaimer.

(21) Appl. No.: 11/789,423

(22) Filed: Apr. 24, 2007

(65) Prior Publication Data
US 2008/0076768 A1 Mar. 27, 2008

Related U.S. Application Data

(60) Provisional application No. 60/794,966, filed on Apr. 26, 2006.

(51) Int. Cl.
A61K 31/535 (2006.01)
C07D 413/14 (2006.01)
(52) U.S. Cl. .................................. 514/234.5; 544/116
(58) Field of Classification Search ................ 544/116; 514/234.5
See application file for complete search history.

(56) References Cited

U.S. PATENT DOCUMENTS

| | | | |
|---|---|---|---|
| 3,475,429 A | 10/1969 | Woitun et al. | |
| 3,661,908 A | 5/1972 | Woitun et al. | |
| 3,763,156 A | 10/1973 | Woitun et al. | |
| 3,838,121 A | 9/1974 | Woitun et al. | |
| 4,007,187 A | 2/1977 | Fauran et al. | |
| 4,146,716 A | 3/1979 | Cox et al. | |
| 4,196,207 A | 4/1980 | Webber et al. | |
| 6,608,053 B2 | 8/2003 | Hayakawa et al. | |
| 6,838,457 B2 | 1/2005 | Hayakawa et al. | |
| 7,037,915 B2 | 5/2006 | Hayakawa et al. | |
| 7,173,029 B2 | 2/2007 | Hayakawa et al. | |

FOREIGN PATENT DOCUMENTS

| | | |
|---|---|---|
| EP | 1277738 A1 | 1/2003 |
| GB | 1393161 | 5/1975 |
| WO | WO 2004/065391 A1 | 8/2004 |
| WO | WO 2006/046031 A1 | 5/2006 |
| WO | WO 2006/046035 A1 | 5/2006 |
| WO | WO 2006/046040 A1 | 5/2006 |

OTHER PUBLICATIONS

Cancer and Metastasis Reviews (1998), 17(1), 91-106.*
Science (1999), vol. 286, 531-537.*
Berge et al., Journal of Pharmaceutical Sciences, vol. 66, No. 1, Jan. 1977, pp. 1-19.*
Briel et al. "Selective Nucleophilic Replacement of the Benzylsulfanyl Group in 2,4-Disulfanyl-substituted Thieno[2,3-d]pyrimidin-6-carboxylic Acid Derivatives by Secondary Amines", Journal Heterocyclic Chem. , 42(5), 841-846, Jul.-Aug. 2005.
Bachman et al., "The PIK3CA gene is mutated with high frequency in human breast cancers", Cancer Biology & Therapy, 3(8), 772-775, Aug. 2004.
Byrn et al., "Hydrates and Solvates", Solid-State Chemistry of Drugs, Second Edition, 233-247, 1999.
C. Garcia-Echeverria et al., "Drug discovery approaches targeting the PI3/Akt pathway in cancer", Oncogene, 27, 5511-5526, 2008.
Kang et al., "Phosphatidylinositol 3-kinase mutations identified in human cancer are oncogenic", PNAS, 102(3), 802-807, Jan. 18, 2005.
Raynaud et al., "Biological properties of potent inhibitors of class I phophatidylinositide 3-kinases: from PI-103 through PI-540, PI-620 to the oral agent GDC-0941", Mol. Cancer Ther., 8(7), 1725-1738, Jul. 2009.
Samuels et al., "High frequency of mutations of the PIK3CA gene in human cancers", Science, 304, 554, Apr. 23, 2004.
Shayesteh et al., "PIK3CA is implicated as an oncogene in ovarian cancer", Nature Genetics, 21, 99-102, Jan. 1999.
Workman et al., "Drugging the PI3 kinome", Nature Biotechnology, 24(7), 794-796, Jul. 2006.
Yap et al., "Targeting the PI3K-AKT-mTOR pathway: progress, pitfalls, and promises", Current Opinion in Pharmacology, 8, 393-412, 2008.

* cited by examiner

Primary Examiner—Rebecca L Anderson
(74) Attorney, Agent, or Firm—Viksnins, Harris & Padys PLLP

(57) ABSTRACT

A thienopyrimidine of formula (I):

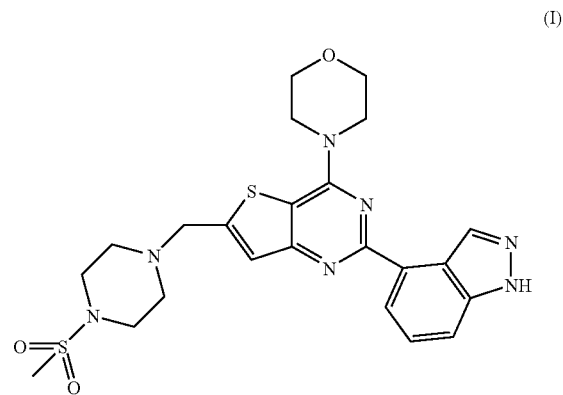

and the pharmaceutically acceptable salts thereof have activity as inhibitors of PI3K with selectivity for the P110α subtype, and may be used to treat diseases and disorders arising from abnormal cell growth, function or behaviour, particularly those associated with PI3 kinase such as cancer, immune disorders, cardiovascular disease, viral infection, inflammation, metabolism/endocrine disorders and neurological disorders. Processes for synthesizing the compounds are also described.

16 Claims, No Drawings

PHARMACEUTICAL COMPOUNDS

PRIORITY OF INVENTION

This application claims priority to U.S. Provisional Application No. 60/794,966 that was filed on 26 Apr. 2006. The entire content of this provisional application is hereby incorporated herein by reference.

FIELD OF THE INVENTION

The present invention relates to pyrimidine derivatives and their use as inhibitors of phosphatidylinositol 3-kinase (PI3K).

BACKGROUND TO THE INVENTION

Phosphatidylinositol (hereinafter abbreviated as "PI") is one of a number of phospholipids found in cell membranes. In recent years it has become clear that PI plays an important role in intracellular signal transduction. In the late 1980s, a PI3 kinase (PI3K) was found to be an enzyme which phosphorylates the 3-position of the inositol ring of phosphatidylinositol (D. Whitman et al, 1988, Nature, 332, 664).

PI3K was originally considered to be a single enzyme, but it has now been clarified that a plurality of subtypes are present in PI3K. Each subtype has its own mechanism for regulating activity. Three major classes of PI3Ks have been identified on the basis of their in vitro substrate specificity (B. Vanhaesebroeck, 1997, Trend in Biol. Sci, 22, 267). Substrates for class I PI3Ks are PI, PI 4-phosphate (PI4P) and PI 4,5-biphosphate (PI (4,5)P2). Class I PI3Ks are further divided into two groups, class Ia and class Ib, in terms of their activation mechanism. Class Ia PI3Ks include PI3K p110α, p110β and p110δ subtypes, which transmit signals from tyrosine kinase-coupled receptors. Class Ib PI3K includes a p101γ subtype activated by a G protein-coupled receptor. PI and PI(4)P are known as substrates for class II PI3Ks. Class II PI3Ks include PI3K C2α, C2β and C2γ subtypes, which are characterized by containing C2 domains at the C terminus. The substrate for class III PI3Ks is PI only.

In the PI3K subtypes, the class Ia subtype has been most extensively investigated to date. The three subtypes of class Ia are heterodimers of a catalytic 110 kDa subunit and regulatory subunits of 85 kDa or 55 kDa. The regulatory subunits contain SH2 domains and bind to tyrosine residues phosphorylated by growth factor receptors with a tyrosine kinase activity or oncogene products, thereby inducing the PI3K activity of the p 110 catalytic subunit which phosphorylates its lipid substrate. Thus, the class Ia subtypes are considered to be associated with cell proliferation and carcinogenesis.

WO 01/083456 describes a series of condensed heteroaryl derivatives which have activity as inhibitors of PI3K and which suppress cancer cell growth.

SUMMARY OF THE INVENTION

It has now been found that a particular thienopyrimidine is a potent inhibitor of PI3K with drug-like physicochemical and pharmacokinetic properties. The compound exhibits selectivity for class Ia PI3Ks over class Ib, in particular for the P110α subtype.

Accordingly, the present invention provides a compound which is a thienopyrimidine of formula (I):

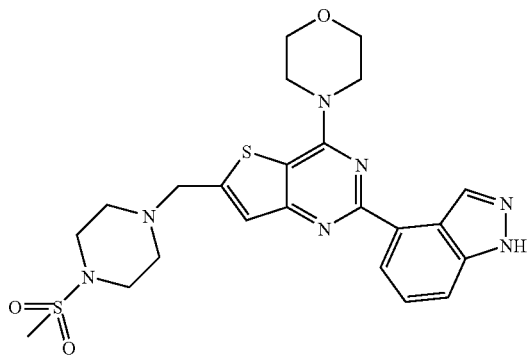

or a pharmaceutically acceptable salt thereof.

DETAILED DESCRIPTION OF THE INVENTION

The thienopyrimidine of formula (I) is 2-(1H-Indazol-4-yl)-6-(4-methanesulfonyl-piperazin-1-ylmethyl)-4-morpholin-4-yl-thieno[3,2-d]pyrimidine A suitable synthetic strategy for producing the compound of the invention employs the precursor carboxaldehyde of formula (II):

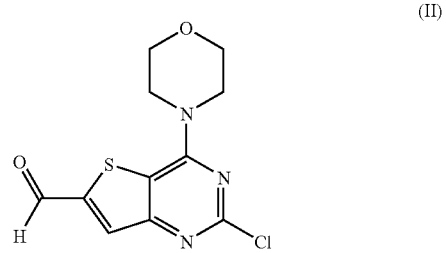

Starting from this precursor the synthesis comprises performing, in either order, a palladium-mediated (Suzuki-type) cross-coupling reaction and a reductive amination. Thus, a compound of the invention may be prepared by a process which comprises:

(a) treating a compound of formula (II):

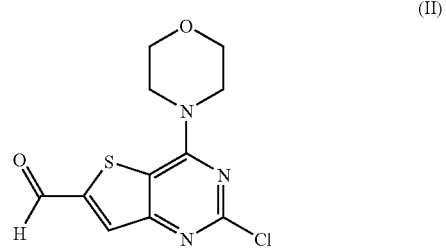

with a boronic acid or ester thereof of formula (IV):

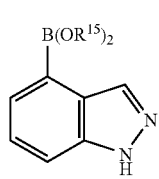
(IV)

in which each $R^{15}$ is H or $C_1$-$C_6$ alkyl or the two groups $OR^{15}$ form, together with the boron atom to which they are attached, a pinacolato boronate ester group, in the presence of a Pd catalyst; and treating the resulting compound of formula (III):

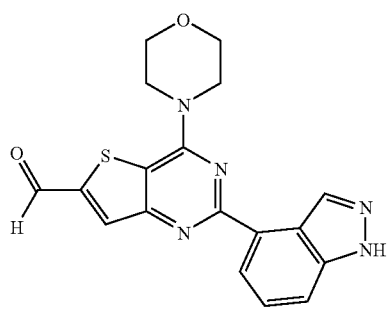
(III)

with an amine of formula (V)

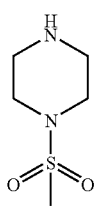
(V)

in the presence of a suitable reducing agent; or (b) treating a compound of formula (II)

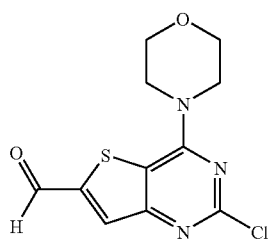
(II)

with an amine of formula (V)

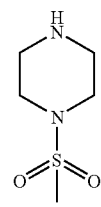
(V)

in the presence of a suitable reducing agent; and treating the resulting compound of formula (VI):

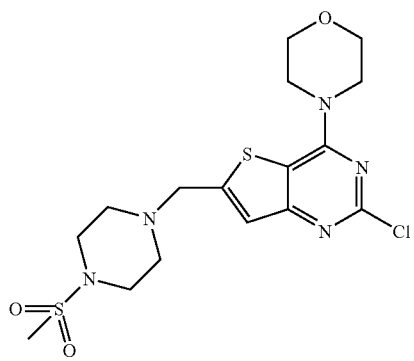
(VI)

with a boronic acid or ester thereof of formula

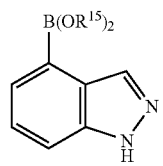
(IV)

in which each $R^{15}$ is H or $C_1$-$C_6$ alkyl or the two groups $OR^{15}$ form, together with the boron atom to which they are attached, a pinacolato boronate ester group, in the presence of a Pd catalyst.

Accordingly, the present invention further provides a process for producing a compound of the invention as defined above, which process comprises treating a compound of formula (III):

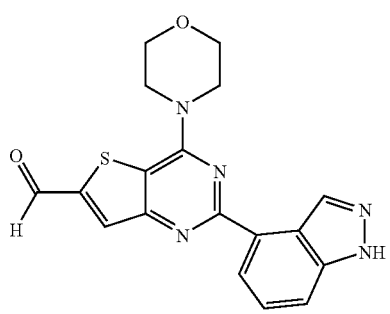
(III)

with an amine of formula (V)

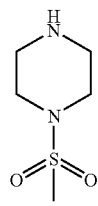
(V)

in the presence of a suitable reducing agent.

The process thus defined may further comprise producing the compound of formula (III) by treating a compound of formula (II):

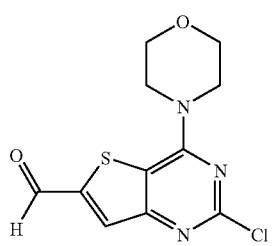
(II)

with a boronic acid or ester thereof of formula (IV):

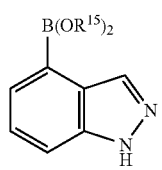
(IV)

in which each $R^{15}$ is H or $C_1$-$C_6$ alkyl or the two groups $OR^{15}$ form, together with the boron atom to which they are attached, a pinacolato boronate ester group, in the presence of a Pd catalyst.

Yet further, the present invention provides a process for producing a compound of the invention as defined above, which process comprises treating a compound of formula (VI):

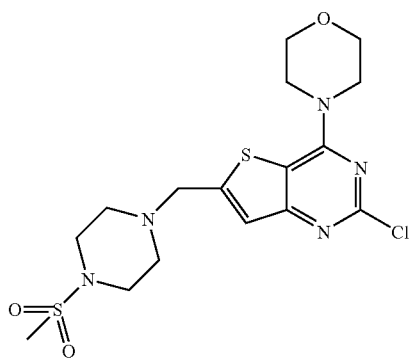
(VI)

with a boronic acid or ester thereof of formula (IV):

(IV)

in which each $R^{15}$ is H or $C_1$-$C_6$ alkyl or the two groups $OR^{15}$ form, together with the boron atom to which they are attached, a pinacolato boronate ester group, in the presence of a Pd catalyst.

The process thus defined may further comprise producing the compound of formula (VI) by treating a compound of formula (II)

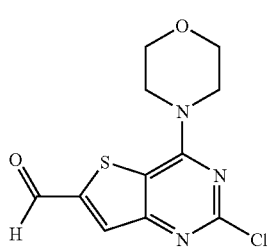
(II)

with an amine of formula (V)

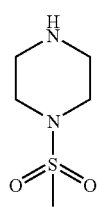
(V)

in the presence of a suitable reducing agent.

A pharmaceutically acceptable salt of a thienopyrimidine of formula (I) may be prepared using conventional techniques. Typically the process comprises treating the thienopyrimidine of formula (I) as defined above with a suitable acid in a suitable solvent.

In the process of the invention as defined above, both the amination step and the Pd-mediated cross-coupling step take place under conventional conditions. The palladium catalyst may be any that is typically used for Suzuki-type cross-couplings, such as $PdCl_2(PPh_3)_2$. The reducing agent is typically a borohydride, for instance $NaBH(OAc)_3$, $NaBH_4$ or $NaCNBH_4$, in particular $NaBH(OAc)_3$.

The pinacolato boronate ester may be, for instance, prepared by a process as described in either of Reference Examples 5 and 6 which follow.

A compound of formula (II) as defined above may be prepared by a process which comprises treating a compound of formula (VII):

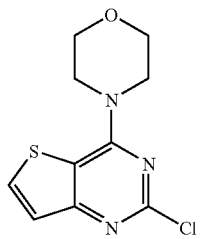

(VII)

with a lithiating agent followed by N,N'-dimethylformamide (DMF). The reaction is typically conducted by adding a solution of the lithiating agent in a non-polar organic solvent, for instance a hydrocarbon solvent such as hexane, to a suspension of the compound of formula (IX) in an organic solvent such as tetrahydrofuran (THF). If THF is used the addition takes place at a low temperature, of about −78° C. The lithiating agent is typically an alkyllithium, for instance n-butyllithium.

A compound of formula (VII) as defined above may be produced by a process which comprises treating a compound of formula (VIII):

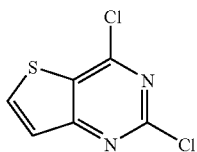

(VIII)

with morpholine in an organic solvent. The solvent is typically an alcohol, such as methanol. The reaction is generally conducted at room temperature.

The compound of formula (VIII) may be prepared by the process described in Reference Example 1, or by analogy with such a process.

A thienopyrimidine of formula (I) may be converted into a pharmaceutically acceptable salt, and a salt may be converted into the free compound, by conventional methods. Examples of pharmaceutically acceptable salts include salts with inorganic acids such as hydrochloric acid, hydrobromic acid, hydroiodic acid, sulphuric acid, nitric acid and phosphoric acid; and organic acids such as methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid. Typically the salt is a mesylate, a hydrochloride, a phosphate, a benzenesulphonate or a sulphate. Most typically the salt is a mesylate or a hydrochloride.

The salts, for instance salts with any of the inorganic or organic acids mentioned above, may be mono-salts or bis-salts. Thus, for example, the mesylate salt may be the mono-mesylate or the bis-mesylate.

The compounds of formula (I) and their salts may exist as hydrates or solvates.

A compound of the present invention has been found in biological tests to be an inhibitor of PI3 kinase. The compound is selective for class Ia PI3 kinases over class Ib and typically exhibits at least a 20-fold selectivity for class Ia over class Ib PI3 kinases. In particular, the compound is selective for the p110α isoform.

A compound of the present invention may thus be used as an inhibitor of PI3 kinase, in particular of a class Ia PI3 kinase. Accordingly, a compound of the present invention can be used to treat a disease or disorder arising from abnormal cell growth, function or behaviour. Such abnormal cell growth, function or behaviour is typically associated with PI3 kinase. Examples of such diseases and disorders are discussed by Drees et al in Expert Opin. Ther. Patents (2004) 14(5):703-732. These include cancer, immune disorders, cardiovascular disease, viral infection, inflammation, metabolism/endocrine disorders and neurological disorders. Examples of metabolism/endocrine disorders include diabetes and obesity.

Examples of cancers which the present compounds can be used to treat include leukaemia, brain tumours, renal cancer, gastric cancer and cancer of the skin, bladder, breast, uterus, lung, colon, prostate, ovary and pancreas. A human or animal patient suffering from an immune disorder, cancer, cardiovascular disease, viral infection, inflammation, a metabolism/endocrine disorder or a neurological disorders may thus be treated by a method comprising the administration thereto of a compound of the present invention as defined above. The condition of the patient may thereby be improved or ameliorated.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. In one embodiment, a human patient is treated with a compound of Formula I and a pharmaceutically acceptable carrier, adjuvant, or vehicle, wherein said compound of Formula I is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

In addition to possessing biochemical potency a compound of the invention exhibits physicochemical and pharmacokinetic properties which makes it particularly well adapted for drug use. This is shown for instance in the results of the biological assays described in Example 3 which follows. In particular the compound possesses high aqueous solubility at physiological pH; the solubility is greater than 100 µM. High solubility at physiological pH is desirable since it promotes bioavailability.

The compound also possesses high metabolic stability, as shown in particular by the hepatocyte clearance assay described in Example 3 in which the compound was shown to have low hepatocyte clearance. Low hepatocyte clearance correlates with a low rate of liver metabolism. It can therefore be seen that the compound of the present invention possess improved physicochemical and pharmacokinetic properties whilst retaining biochemical potency as an inhibitor of PI3 kinase.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

Typically a dose to treat human patients may range from about 10 mg to about 1000 mg of a compound of the invention. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

A compound is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspensions.

F) Vaginally, in the form of pessaries, tampons, creams, gels, pastes, foams or spray formulations containing in addition to the active ingredient such carriers as are known in the art to be appropriate.

Sustained-release preparations of a compound of the invention may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxy-ethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

A compound of the invention may be employed alone or in combination with other therapeutic agents for the treatment of a disease or disorder described herein, such as a hyperproliferative disorder (e.g., cancer). In certain embodiments, a compound of the invention is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of the invention such that they do not adversely affect each other. Such compounds are suitably present in combination in amounts that are effective for the purpose intended. In one embodiment, a composition of this invention comprises a compound of the invention, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The invention will be further described in the Examples which follow:

REFERENCE EXAMPLE 1

2,4-Dichloro-thieno[3,2-d]pyrimidine (VIII)

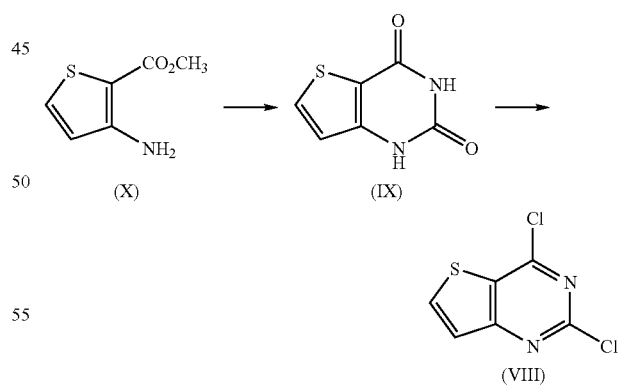

A mixture of methyl 3-amino-2-thiophenecarboxylate (13.48 g, 85.85 mmol) and urea (29.75 g, 5 eq.) was heated at 190° C. for 2 h. The hot reaction mixture was then poured onto sodium hydroxide solution and any insoluble material removed by filtration. The mixture was then acidified (HCl, 2N) to yield H-thieno[3,2-d]pyrimidine-2,4-dione (IX) as a white precipitate, which was collected by filtration and air dried (9.49 g, 66%).

$^1$H NMR (400 MHz, d$_6$-DMSO) 6.90 (1H, d, J=5.2 Hz), 8.10 (1H, d, J=5.2 Hz), 11.60-11.10 (2H, br s).

A mixture of 1H-thieno[3,2-d]pyrimidine-2,4-dione (9.49 g, 56.49 mmol) and phosphorous oxychloride (150 mL) was heated at reflux for 6 h. The reaction mixture was then cooled and poured onto ice/water with vigorous stirring yielding a precipitate. The mixture was then filtered to yield 2,4-dichloro-thieno[3,2-d]pyrimidine (VIII) as a white solid (8.68 g, 75%)

$^1$H NMR (400 MHz, CDCl$_3$) 7.56 (1H, d, J=5.5 Hz), 8.13 (1H, d, J=5.5 Hz).

REFERENCE EXAMPLE 2

2-Chloro-4-morpholin-4-yl-thieno[3,2-d]pyrimidine (VII)

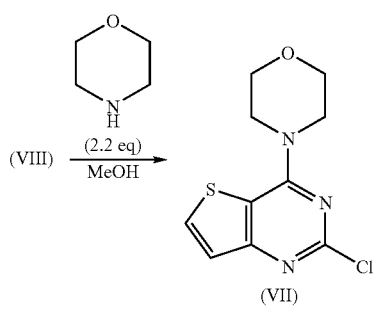

A mixture of 2,4-dichloro-thieno[3,2-d]pyrimidine (VIII), (8.68 g, 42.34 mmol), morpholine (8.11 mL, 2.2 eq.) and MeOH (150 mL) was stirred at room temperature for 1 h. The reaction mixture was then filtered, washed with water and MeOH, to yield the title compound as a white solid (11.04 g, 100%).

$^1$H NMR (400 MHz, d$_6$-DMSO) 3.74 (4H, t, J=4.9 Hz), 3.90 (4H, t, J=4.9 Hz), 7.40 (1H, d, J=5.6 Hz), 8.30 (1H, d, J=5.6 Hz).

REFERENCE EXAMPLE 3

2-Chloro-4-morpholin-4-yl-thieno[3,2-d]pyrimidine-6-carbaldehyde (II)

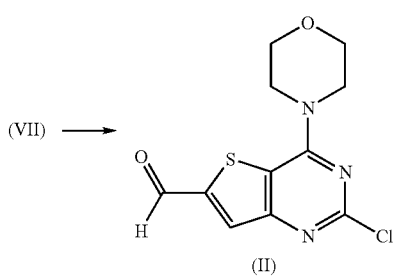

To a suspension of 2-chloro-4-morpholin-4-yl-thieno[3,2-d]pyrimidine (VII) (1.75 g, 6.85 mmol) in dry THF (40 mL) at −78° C. was added a 2.5M solution of nBuLi in hexane (3.3 mL, 1.2 eq.). After stirring for 1 h, dry DMF (796 µL, 1.5 eq.) was added. The reaction mixture was stirred for 1 h at −78° C. and then warmed slowly to room temperature. After a further 2 h at room-temperature the reaction mixture poured onto ice/water yielding a yellow precipitate. This was collected by filtration and air-dried to yield the title compound (1.50 g, 77%)

$^1$H NMR (400 MHz, d$_6$-DMSO) 3.76 (4H, t, J=4.9), 3.95 (4H, t, J=4.9), 8.28 (1H, s), 10.20 (1H, s).

REFERENCE EXAMPLE 4

2-Chloro-6-(4-methanesulfonyl-piperazin-1-ylmethyl)-4-morpholin-4-yl-thieno[3,2-d]yrimidine (VI)

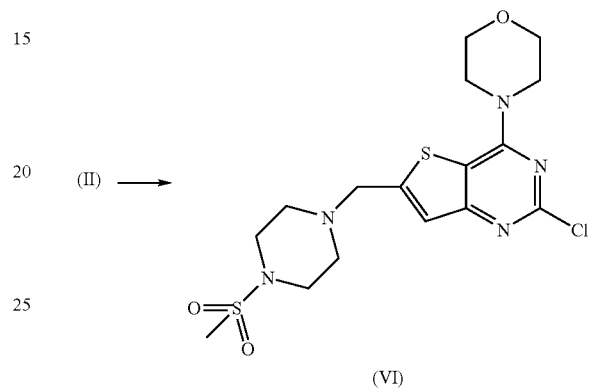

N—BOC-piperazine and methanesulfonyl chloride were reacted together in dichloromethane and triethylamine to yield 4-methanesulfonyl-piperazine-1-carboxylic acid tert-butyl ester. Cleavage of the BOC protecting group using HCl (2M) in dichloromethane yielded 1-methanesulfonyl-piperazine. HCl salt.

A mixture of 2-chloro-4-morpholin-4-yl-thieno[3,2-d]pyrimidine-6-carbaldehyde (II) (1.00 g), 1-methanesulfonyl-piperazine (750 mg) and trimethylorthoformate (3.80 mL) was stirred in 1,2-dichloroethane (30 mL) for 6 hrs at room temperature. To this was added sodium triacetoxyborohydride (900 mg) and the reaction mixture was stirred for 24 hours at room temperature. The mixture was then quenched with brine, extracted with dichloromethane, dried (MgSO$_4$) and the solvent removed in vacuo. The residue was triturated with hot ethyl acetate to yield the title compound (VI) as a white solid (1.01 g).

REFERENCE EXAMPLE 5

4-(4,4,5,5-Tetramethyl-[1,3,2]dioxaborolan-2-yl)-1H-indazole (IVa)

Route 1

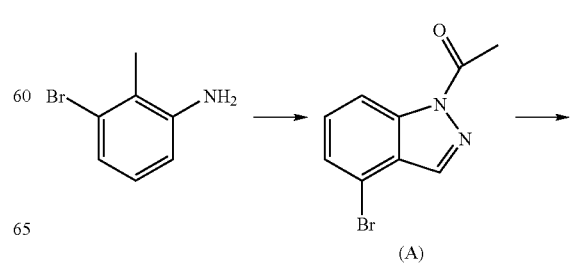

-continued

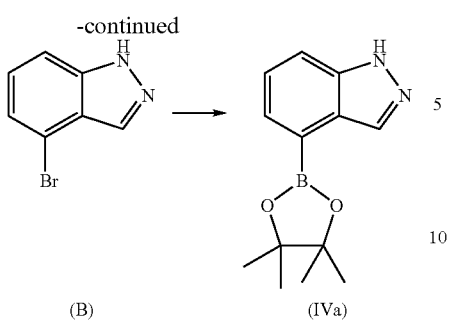

(B)     (IVa)

To a solution of 3-bromo-2-methyl aniline (5.0 g, 26.9 mmol) in chloroform (50 mL) was added potassium acetate (1.05 eq., 28.2 mmol, 2.77 g). Acetic anhydride (2.0 eq., 53.7 mmol, 5.07 mL) was added with concurrent cooling in ice-water. The mixture was then stirred at room temperature for 10 minutes after which time a white gelatinous solid formed. 18-Crown-6 (0.2 eq., 5.37 mmol, 1.42 g) was then added followed by iso-amyl nitrite (2.2 eq., 59.1 mmol, 7.94 mL) and the mixture was heated under reflux for 18 h. The reaction mixture was allowed to cool, and was partitioned between chloroform (3×100 mL) and saturated aqueous sodium hydrogen carbonate (100 mL). The combined organic extracts were washed with brine (100 mL), separated and dried (MgSO$_4$).

The crude product was evaporated onto silica and purified by chromatography eluting with 20%→40% EtOAc-petrol to give 1-(4-bromo-indazol-1-yl)-ethanone (A) (3.14 g, 49%) as an orange solid, and 4-bromo-1H-indazole (B) (2.13 g, 40%) as a pale orange solid.

A: $^1$H NMR (400 MHz, CDCl$_3$) 2.80 (3H, s), 7.41 (1H, t, J=7.8 Hz), 7.50 (1H, d, J=7.8 Hz), 8.15 (1H, s), 8.40 (1H, d, J=7.8 Hz).

B: $^1$H NMR (400 MHz, CDCl$_3$) 7.25 (1H, t, J=7.3 Hz), 7.33 (1H, d, J=7.3 Hz), 7.46 (1H, d, J=7.3 Hz), 8.11 (1H, s), 10.20 (1H, br s),

To a solution of the 1-(4-bromo-indazol-1-yl)-ethanone (3.09 g, 12.9 mmol) in MeOH (50 mL) was added 6N aqueous HCl (30 mL) and the mixture was stirred at room temperature for 7 h. The MeOH was evaporated and the mixture partitioned between EtOAc (2×50 mL) and water (50 mL). The combined organic layers were washed with brine (50 mL), separated and dried (MgSO$_4$). The solvent was removed by evaporation under reduced pressure to give 4-bromo-1H-indazole (2.36 g, 93%).

To a solution of the 4-bromo-1H-indazole (500 mg, 2.54 mmol) and bis(pinacolato)diboron (1.5 eq., 3.81 mmol) in DMSO (20 mL) was added potassium acetate (3.0 eq., 7.61 mmol, 747 mg; dried in drying pistol) and PdCl$_2$(dppf)$_2$ (3 mol %, 0.076 mmol, 62 mg). The mixture was degassed with argon and heated at 80° C. for 40 h. The reaction mixture was allowed to cool and partitioned between water (50 mL) and ether (3×50 mL). The combined organic layers were washed with brine (50 mL), separated and dried (MgSO$_4$). The crude material was purified by chromatography eluting with 30%→40% EtOAc-petrol to give an inseparable 3:1 mixture of the 4-(4,4,5,5-tetramethyl-[1,3,2]dioxaborolan-2-yl)-1H-indazole (369 mg, 60%) and indazole (60 mg, 20%); the title compound (IVa) was isolated as a yellow gum which solidified upon standing to furnish as an off-white solid.

$^1$H NMR (400 MHz, d$_6$-DMSO) 1.41 (12H, s), 7.40 (1H, dd, J=8.4 Hz, 6.9 Hz), 7.59 (1H, d, J=8.4 Hz), 7.67 (1H, d, J=6.9 Hz), 10.00 (1H, br s), 8.45 (1H, s), and indazole: 7.40 (1H, t), 7.18 (1H, t, J=7.9 Hz), 7.50 (1H, d, J=9.1 Hz), 7.77 (1H, d, J=7.9 Hz), 8.09 (1H, s). Impurity at 1.25.

REFERENCE EXAMPLE 6

4-(4,4,5,5-Tetramethyl-[1,3,2]dioxaborolan-2-yl)-1H-indazole (IVa)

Route 2

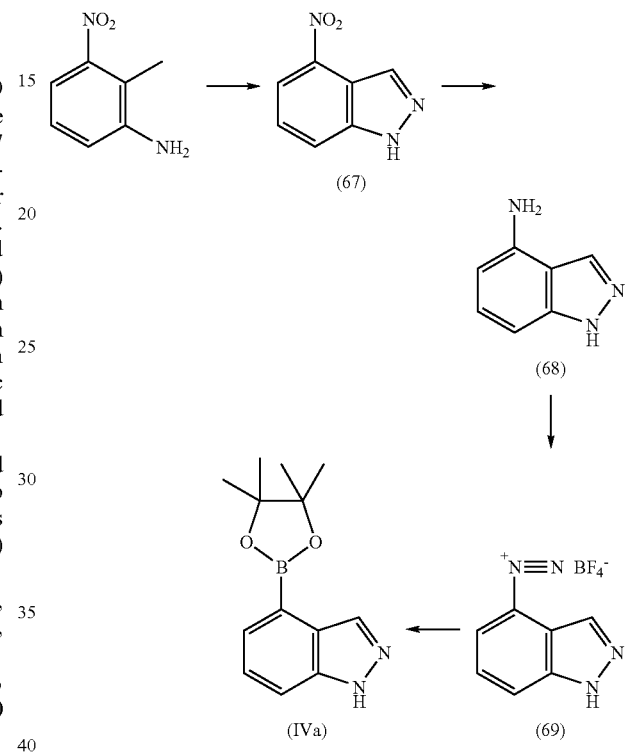

To a solution of 2-methyl-3-nitroaniline (2.27 g, 14.91 mmol) in acetic acid (60 mL) was added a solution of sodium nitrite (1.13 g, 1.1 eq.) in water (5 mL). After 2 h, the deep red solution was poured onto ice/water and the resulting precipitate collected by filtration to yield 4-nitro-1H-indazole (67) (1.98 g, 81%).

A mixture of 4-nitro-1H-indazole (760 mg, 4.68 mmol), palladium on charcoal (10%, cat.) and ethanol (30 mL) was stirred under a balloon of hydrogen for 4 h. The reaction mixture was then filtered through celite, and the solvent removed in vacuo to yield 1H-indazol-4-ylamine (68) (631 mg, 100%).

An aqueous solution of sodium nitrite (337 mg, 4.89 mmol) in water (2 mL) was added dropwise to a suspension of 1H-indazol-4-ylamine (631 mg, 4.74 mmol) in 6M hydrochloric acid (7.2 mL) at below 0° C. After stirring for 30 minutes, sodium tetrafluorobrate (724 mg) was added to the reaction mixture. A viscous solution resulted, which was filtered and washed briefly with water to yield 1H-indazole-4-diazonium tetrafluoroborate salt (69) (218 mg, 20%) as a deep red solid.

Dry MeOH (4 mL) was purged with argon for 5 minutes. To this was added 1H-indazole-4-diazonium tetrafluoroborate salt (218 mg, 0.94 mmol), bis-pinacolato diboron (239 mg, 1.0 eq.) and [1,1'-bis(diphenylphosphino)ferrocene]palladium (II) chloride (20 mg). The reaction mixture was stirred for 5 h and then filtered through celite. The residue was purified using flash chromatography to yield the desired title compound (IVa), (117 mg).

REFERENCE EXAMPLE 7

2-(1H-Indazol-4-yl)-4-morpholin-4-yl-thieno[32-d]pyrimidine-6-carbaldehyde (III)

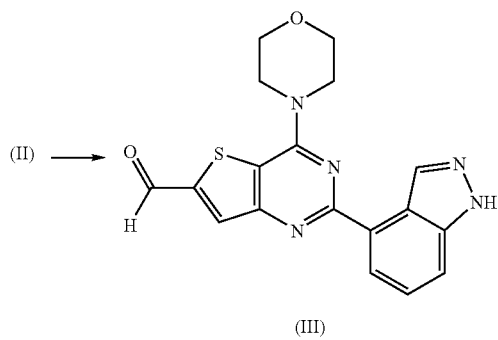

(III)

A mixture of 2-chloro-4-morpholin-4-yl-thieno[3,2-d]pyrimidine-6-carbaldehyde (II) (100 mg, 0.35 mmol), 4-(4,4,5,5-tetramethyl-[1,3,2]dioxaborolan-2-yl)-1H-indazole (70) (95 mg, 0.39 mmol) and sodium carbonate (112 mg) were suspended in toluene (2.5 mL), ethanol (1.5 mL) and water (0.7 mL). To this was added bis(triphenylphosphine)palladium(II) chloride (13.5 mg) and the reaction vessel was flushed with argon. The reaction mixture was microwaved at 120° C. for 1 h and then partitioned between DCM and water, the organic layer was washed with brine, dried over magnesium sulfate, filtered and evaporated in vacuo. The resulting residue was purified using flash chromatography to yield the title compound (III) (97 mg).

EXAMPLE 1

2-(1H-indazol-4-yl)-6-(4-methanesulfonyl-piperazin-1-ylmethyl)-4-morpholin-4-yl-thieno[3,2-d]pyrimidine (I)

A mixture of 2-chloro-6-(4-methanesulfonyl-piperazin-1-ylmethyl)-4-morpholin-4-yl-thieno[3,2-d]pyrimidine (2.00 g), 4-(4,4,5,5-tetramethyl-[1,3,2]dioxaborolan-2-yl)-1H-indazole (2.26 g), toluene (24 mL), ethanol (12 mL), water (6 mL), sodium carbonate (1.72 g) and PdCl$_2$(PPh$_3$)$_2$ (325 mg) was heated to 130° C. in the microwave for 90 minutes.

The reaction mixture was cooled, diluted with chloroform, washed with brine, dried (MgSO$_4$) and the solvent removed in vacuo. The residue was purified using flash chromatography (ethyl acetate then 5% ethyl acetate/methanol) and then trituration with ether yielded the desired the desired title compound (1.4 g) MS data: (ESI+): MH+514

NMR data: (CDCl3): 2.67-2.71 (4H, m), 2.81 (3H, s), 3.29-3.33 (4H, m), 3.89 (2H, s), 3.89-3.93 (4H, m), 4.08-4.12 (4H, m), 7.41 (1H, s), 7.51 (1H, t, J=7.2), 7.60 (1H, d, J=8.3), 8.28 (1H, d, J=7.5), 9.02 (1H, s), 10.10 (1H, br)

EXAMPLE 2

2-(1H-indazol-4-yl)-6-(4-methanesulfonyl-piperazin-1-ylmethyl)-4-morpholin-4-yl-thieno[3,2-d]pyrimidine bismesylate To 2-(1H-indazol-4-yl)-6-(4-methanesulfonyl-piperazin-1-ylmethyl)-4-morpholin-4-yl-thieno[3,2-d]pyrimidine (2.00 g, 3.89 mmol) in dichloromethane (50 ml) and methanol (20 ml) was added methanesulfonic acid (2 equiv., 505 ul). The reaction mixture was stirred for 3 hours at room temperature during which time a white precipitate gradually crashed out. Volatiles were removed in vacuo, the residue was triturated with diethyl ether, the solvent decanted and the solid dried under vacuum to give the title compound (2.70 g).

NMR (400 MHz, DMSO). Includes the following signals 2.32 (s, 6H), 3.00 (s, 3H), 3.84-3.86 (4H, m). 4.09-4.11 (4H, m), 8.8)(1H, s).

EXAMPLE 3

Biological Testing

A compound of the invention, prepared as described above, was submitted to the following series of biological assays:

(i) PI3K Biochemical Screening

Compound inhibition of PI3K was determined in a radiometric assay using purified, recombinant enzyme and ATP at a concentration of 1 uM. The compound was serially diluted in 100% DMSO. The kinase reaction was incubated for 1 h at room temperature, and the reaction was terminated by the addition of PBS. IC$_{50}$ values were subsequently determined using sigmoidal dose-response curve fit (variable slope). The compound had an IC$_{50}$ against PI3K of less than 0.1 µM.

(ii) Cellular Proliferation Inhibition

Cells were seeded at optimal density in a 96 well plate and incubated for 4 days in the presence of test compound. Alamar Blue® was subsequently added to the assay medium, and cells were incubated for 6 h before reading at 544 nm excitation, 590 nm emission. EC$_{50}$ values were calculated using a sigmoidal dose response curve fit. The compound had an EC$_{50}$ of 50 uM or less in the range of cell lines utilized.

(iii) Caco-2 Permeability

Caco-2 cells were seeded onto Millipore Multiscreen plates at 1×10$^5$ cells/cm$^2$, and were cultured for 20 days. Assessment of compound permeability was subsequently conducted. The compounds were applied to the apical surface (A) of cell monolayers and compound permeation into the basolateral (B) compartment was measured. This was performed in the reverse direction (B-A) to investigate active transport. A permeability coefficient value, P$_{app}$, for each compound, a measure of the rate of permeation of the compound across the membrane, was calculated. Compounds were grouped into low (P$_{app}$</=1.0×10$^6$ cm/s) or high (P$_{app}$>/=1.0×10$^6$ cm/s) absorption potential based on comparison with control compounds with established human absorption.

For assessment of a compound's ability to undergo active efflux, the ratio of basolateral (B) to apical (A) transport compared with A to B was determined. Values of B-A/A-B>/= 1.0 indicated the occurrence of active cellular efflux. The had P$_{app}$ values>/=1.0×10$^6$ cm/s.

(iv) Hepatocyte Clearance

Suspensions of cryopreserved human hepatocytes were used. Incubations were performed at compound concentration of 1 mM or 3 µM at a cell density of 0.5×10⁶ viable cells/mL. The final DMSO concentration in the incubation was 0.25%. Control incubations were also performed in the absence of cells to reveal any non-enzymatic degradation. Duplicate samples (50 µL) were removed from the incubation mixture at 0, 5, 10, 20, 40 and 60 minutes (control sample at 60 minutes only) and added to MeOH—containing internal standard (100 µL)—to terminate the reaction. Tolbutamide, 7-hydroxycoumarin, and testosterone were used as control compounds. Samples were centrifuged and the supernatants at each time point pooled for analysis by LC-MSMS. From a plot of ln peak area ratio (parent compound peak area/internal standard peak area) against time, intrinsic clearance ($CL_{int}$) was calculated as follows: $CL_{int}$ (µl/min/million cells)=V×k, where k is the elimination rate constant, obtained from the gradient of ln concentration plotted against time; V is a volume term derived from the incubation volume and is expressed as uL $10^6$ cells$^{-1}$.

On the basis of low (CL</=4.6 µL/min/$10^6$ cells), medium (CL>/=4.6; </=25.2 µl/min/$10^6$ cells) and high (>/=25.2 µl/min/$10^6$ cells) clearance, the compound of the invention was determined to have low hepatocyte clearance.

(v) Cytochrome P450 Inhibition

The compound of the invention was screened against five CYP450 targets (1A2, 2C9, 2C19, 2D6, 3A4) at 10 concentrations in duplicate, with a top concentration of 100 uM being used. Standard inhibitors (furafylline, sulfaphenazole, tranylcypromine, quinidine, ketoconazole) were used as controls. Plates were read using a BMG LabTechnologies PolarStar in fluorescence mode. The compound displayed weak activity ($IC_{50}$>/=5 uM) against all isoforms of CYP450.

(vi) Cytochrome P450 Induction

Freshly isolated human hepatocytes from a single donor were cultured for 48 h prior to addition of test compound at three concentrations and were incubated for 72 h. Probe substrates for CYP3A4 and CYP1A2 were added for 30 minutes and 1 h before the end of the incubation. At 72 h, cells and media were removed and the extent of metabolism of each probe substrate quantified by LC-MS/MS. The experiment was controlled by using inducers of the individual P450s incubated at one concentration in triplicate. The compound of the invention showed negligible effects on induction of cytochrome P450 enzymes.

(vii) Plasma Protein Binding

Solutions of test compound (5 um, 0.5% final DMSO concentration) were prepared in buffer and 10% plasma (v/v in buffer). A 96 well HT dialysis plate was assembled so that each well was divided in two by a semi-permeable cellulose membrane. The buffer solution was added to one side of the membrane and the plasma solution to the other side; incubations were then conducted at 37° C. over 2 h in triplicate. The cells were subsequently emptied, and the solutions for each batch of compounds were combined into two groups (plasma-free and plasma-containing) then analysed by LC-MSMS using two sets of calibration standards for plasma-free (6 points) and plasma-containing solutions (7 points). The fraction unbound value for the compound was calculated: highly protein bound compounds (>/=90% bound) had an Fu</=0.1. The compound of the invention had an Fu value>/=0.1.

(viii) hERG Channel Blockage

The compound of the invention was evaluated for its ability to modulate rubidium efflux from HEK-294 cells stably expressing hERG potassium channels using established flux methodology. Cells were prepared in medium containing RbCl and were plated into 96-well plates and grown overnight to form monolayers. The efflux experiment was initiated by aspirating the media and washing each well with 3×100 µL of pre-incubation buffer (containing low [K⁺]) at room temperature. Following the final aspiration, 50 µL of working stock (2×) compound was added to each well and incubated at room temperature for 10 minutes. 50 µL of stimulation buffer (containing high [K+]) was then added to each well giving the final test compound concentrations. Cell plates were then incubated at room temperature for a further 10 minutes. 80 µL of supernatant from each well was then transferred to equivalent wells of a 96-well plate and analysed via atomic emission spectroscopy. The compound was screened as 1 pt duplicate $IC_{50}$ curves, n=2, from a top concentration of 100 µM.

EXAMPLE 4

Tablet Composition

Tablets, each weighing 0.15 g and containing 25 mg of a compound of the invention are manufactured as follows:

Composition for 10,000 Tablets
Active compound (250 g)
Lactose (800 g)
Corn starch (415 g)
Talc powder (30 g)
Magnesium stearate (5 g)

The active compound, lactose and half of the corn starch are mixed. The mixture is then forced through a sieve 0.5 mm mesh size. Corn starch (10 g) is suspended in warm water (90 mL). The resulting paste is used to granulate the powder. The granulate is dried and broken up into small fragments on a sieve of 1.4 mm mesh size. The remaining quantity of starch, talc and magnesium is added, carefully mixed and processed into tablets.

EXAMPLE 5

Injectable Formulation

| Formulation A | |
|---|---|
| Active compound | 200 mg |
| Hydrochloric Acid Solution 0.1M or Sodium Hydroxide Solution 0.1M q.s. to pH | 4.0 to 7.0 |
| Sterile water q.s. to | 10 mL |

The compound of the invention is dissolved in most of the water (35° 40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

| Formulation B | |
|---|---|
| Active Compound | 125 mg |
| Sterile, Pyrogen-free, pH 7 Phosphate Buffer, q.s. to | 25 mL |
| Active compound | 200 mg |
| Benzyl Alcohol | 0.10 g |

-continued

| Formulation B | |
|---|---|
| Glycofurol 75 | 1.45 g |
| Water for injection q.s to | 3.00 mL |

The active compound is dissolved in the glycofurol. The benzyl alcohol is then added and dissolved, and water added to 3 mL. The mixture is then filtered through a sterile micropore filter and sealed in sterile 3 mL glass vials (type 1).

EXAMPLE 6

Syrup Formulation

| Active compound | 250 mg |
|---|---|
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention is dissolved in a mixture of the glycerol and most of the purified water. An aqueous solution of the sodium benzoate is then added to the solution, followed by addition of the sorbital solution and finally the flavour. The volume is made up with purified water and mixed well.

The invention claimed is:

1. A compound which is a thienopyrimidine of formula (I):

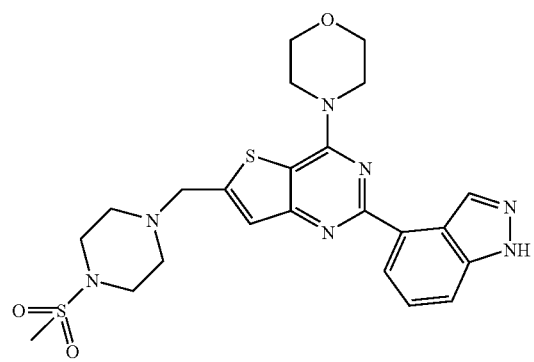

(I)

or a pharmaceutically acceptable salt thereof.

2. A compound according to claim 1 wherein the pharmaceutically acceptable salt is selected from salts with hydrochloric acid, hydrobromic acid, hydroiodic acid, sulphuric acid, nitric acid, phosphoric acid, methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.

3. A compound according to claim 1 wherein the pharmaceutically acceptable salt is a mono-salt or a bis-salt.

4. A compound according to claim 1 which is a mono-salt or a bis-salt with methanesulphonic acid, benzenesulphonic acid, hydrochloric acid, phosphoric acid and sulphuric acid.

5. A compound according to claim 1 which is 2-(1H-indazol-4-yl)-6-(4-methanesulfonyl-piperazin-1-ylmethyl)-4-morpholin-4-yl-thieno[3,2-d]pyrimidine bismesylate.

6. A process for producing a compound as defined in claim 1, which process comprises treating a compound of formula (III):

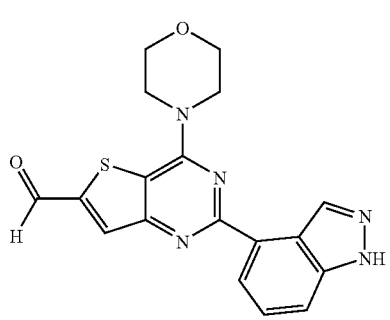

(III)

with an amine of formula (V)

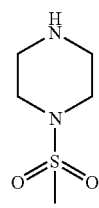

(V)

in the presence of a suitable reducing agent.

7. A process according to claim 6 which further comprises producing the compound of formula (III) by treating a compound of formula (II):

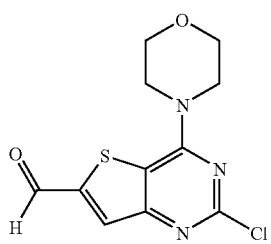

(II)

with a boronic acid or ester thereof of formula (IV):

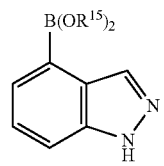

(IV)

in which each $R^{15}$ is H or $C_1$-$C_6$ alkyl or the two groups $OR^{15}$ form, together with the boron atom to which they are attached, a pinacolato boronate ester group, in the presence of a Pd catalyst.

8. A process for producing a compound as defined in claim 1, which process comprises treating a compound of formula (VI)

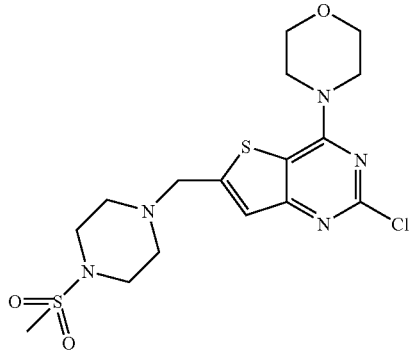

with a boronic acid or ester thereof of formula (IV):

in which each $R^{15}$ is H or $C_1$-$C_6$ alkyl or the two groups $OR^{15}$ form, together with the boron atom to which they are attached, a pinacolato boronate ester group, in the presence of a Pd catalyst.

9. A process according to claim 8, which further comprises producing the compound of formula (VI) by treating a compound of formula (II)

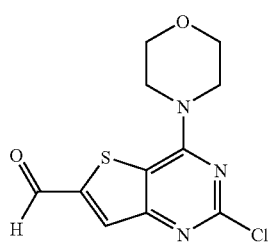

with an amine of formula (V)

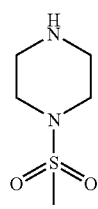

in the presence of a suitable reducing agent.

10. A process for producing a pharmaceutically acceptable salt as defined in claim 1, which process comprises treating a thienopyrimidine of formula (I):

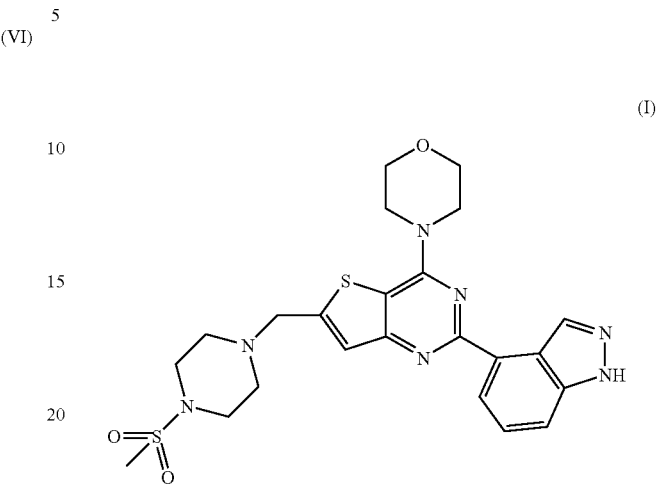

with a suitable acid in a suitable solvent.

11. A process according to claim 10, wherein the acid is selected from hydrochloric acid, hydrobromic acid, hydroiodic acid, sulphuric acid, nitric acid, phosphoric acid, methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.

12. A process according to claim 10 wherein the acid is selected from methanesulphonic acid, benzenesulphonic acid, hydrochloric acid, phosphoric acid and sulphuric acid.

13. A pharmaceutical composition which comprises a pharmaceutically acceptable carrier or diluent and, as an active ingredient, a compound as claimed in claim 1.

14. A composition according to claim 13 which is formulated for oral administration.

15. A process for producing a pharmaceutical composition which process comprises combining a compound as defined in claim 1 with a pharmaceutically acceptable carrier.

16. A kit comprising:
(a) a first pharmaceutical composition comprising a compound as defined in claim 1;
(b) a second pharmaceutical composition that comprises a compound having anti-hyperproliferative activity; and
(c) instructions for the simultaneous, sequential or separate administration of said first and second pharmaceutical compositions to a patient in need thereof;
wherein said first and second pharmaceutical compositions are contained in separate containers.

* * * * *